United States Patent
Kroll

(10) Patent No.: US 6,766,194 B1
(45) Date of Patent: *Jul. 20, 2004

(54) DYNAMIC CONTROL OF OVERDRIVE PACING BASED ON DEGREE OF RANDOMNESS WITHIN HEART RATE

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 340 days.

This patent is subject to a terminal disclaimer.

(21) Appl. No.: 10/017,935

(22) Filed: Dec. 12, 2001

(51) Int. Cl.[7] ............................................. A61N 1/362

(52) U.S. Cl. ............................................. 607/9; 607/4

(58) Field of Search ........................... 607/4, 5, 9, 12, 607/14, 15; 600/513, 515, 518

(56) References Cited

U.S. PATENT DOCUMENTS

| 4,712,555 | A | | 12/1987 | Thornander et al. ... 128/419 PG |
|---|---|---|---|---|
| 4,940,052 | A | | 7/1990 | Mann et al. .......... 128/419 PG |
| 4,944,298 | A | | 7/1990 | Sholder ................ 128/419 PG |
| 5,042,497 | A | | 8/1991 | Shapland .................... 128/696 |
| 5,201,321 | A | | 4/1993 | Fulton ........................ 128/702 |
| 5,342,401 | A | | 8/1994 | Spano et al. .................... 607/5 |
| 5,447,520 | A | | 9/1995 | Spano et al. .................... 607/5 |
| 5,466,254 | A | | 11/1995 | Helland ....................... 607/123 |
| 5,476,483 | A | | 12/1995 | Bornzin et al. .............. 607/17 |
| 5,609,158 | A | | 3/1997 | Chan .......................... 128/708 |
| 5,676,690 | A | | 10/1997 | Noren .......................... 607/9 |
| 5,690,688 | A | | 11/1997 | Norén et al. ................. 607/17 |
| 5,713,929 | A | * | 2/1998 | Hess et al. ..................... 607/14 |
| 5,730,144 | A | | 3/1998 | Katz et al. ................... 128/713 |
| 5,817,132 | A | | 10/1998 | Karagueuzian et al. ........ 607/5 |
| 6,058,328 | A | | 5/2000 | Levine et al. ................. 607/14 |
| 6,192,273 | B1 | | 2/2001 | Igel et al. ..................... 607/14 |
| 6,308,094 | B1 | | 10/2001 | Shusterman et al. ........ 600/516 |
| 6,519,493 | B1 | * | 2/2003 | Florio et al. ................... 607/9 |
| 6,694,188 | B1 | * | 2/2004 | Kroll .......................... 607/14 |

OTHER PUBLICATIONS

Callaway et al., "Scaling Exponent Predicts Defibrillation Success for Out–of–Hospital Ventricular Fibrillation Cardiac Arrest", Circulation, pp 1656–1661 (Mar. 27, 2001.
Cotton, "Chaos, Other Nonlinear Dynamics Research May Have Answers, Applications for Clinical Medicine", JAMA, vol. 266, No. 1, pp: 12–18 (Jul. 3, 1991).
Klonowski, "Signal and Image Analysis Using Chaos Theory and Fractal Geometry", Machine Graphics & Vision, vol. 9 (1/2), pp: 403–413 (2000).
Kroll et al., "Slope Filtered Pointwise Correlation Dimension Algorithm and Its Evaluation With Prefibrillation Heart Rate Data", Journal of Electrocardiology, vol. 24, Supplement, pp: 97–101 (1991).
Mäkikallio, et al., "Abnormalities in Beat to Beat Complexity of Heart Rate Dynamics in Patients with a Previous Myocardial Infarction", JACC, vol. 28, No. 4, pp:1005–1011 (Oct. 1996).
Peng et al., "Quantification of Scaling Exponents and Crosssover Phenomena in Nonstationary Heartbeat Time Series", Chaos, vol. 5, No. 1, pp: 82–87 (1995).

(List continued on next page.)

Primary Examiner—George Manuel

(57) ABSTRACT

A degree of randomness associated with the heart rate of the patient is determined based on an analysis of electrical heart signals. The degree of randomness may be determined, for example, based on a degree of entropy or a chaos dimensionality associated with heart rate. If the degree of randomness falls below a threshold value, indicating that the heart rate may be too coherent, a warning signal is generated indicating a significant risk of onset of a tachyarrhythmia. To prevent the tachyarrhythmia from occurring, overdrive pacing is initiated or, if already initiated, the overdrive pacing is made more aggressive. In a related technique, chaotic pacing is performed to ensure a sufficient heart rate variability.

23 Claims, 6 Drawing Sheets

OTHER PUBLICATIONS

Peng et al., "Fractal Analysis Methods", Reprinted from Nonlinear Dynamics, Self–Organization, and Biomedicine, J. Walleczek, ed., Cambridge University Press, (2000).

Pincus, "Approximate Entropy as a Measure of System Complexity", Proc. Natl. Acad. Sci. USA, vol. 88, pp: 2297–2301 (Mar. 1991).

Richman et al., "Physiological Time–Series Analysis Using Approximate Entropy and Sample Entropy", Am. J. Physiol. Heart Circ, 278, pp: H2039–H2049 (2000).

Vikman, et al., "Altered Complexity and Correlation Properties of R–R Interval Dynamics Before Spontaneous Onset of Paroxsymal Atrial Fibrillation", Circulation, pp: 2079–2084 (Nov. 16, 1999).

Vikman, et al., "Differences in Heart Rate Dynamics Before the Spontaneous Onset of Long and Short Episodes of Paroxysmal Atrial Fibrillation", A.N.E., vol. 6, No. 2, pp: 134–142 (Apr. 2001).

Laitio, et al., "Correlation Properties and Complexity of Perioperative RR–Interval Dynamics in Coronary Artery Bypass Surgery Patients", Anesthesiology, vol. 93, No. 1, pp: 69–80 (Jul. 2000).

* cited by examiner

DYNAMIC CONTROL OF OVERDRIVE PACING BASED ON DEGREE OF RANDOMNESS WITHIN HEART RATE

CROSS-REFERENCE TO RELATED APPLICATIONS

This application is related to copending U.S. Patent Applications: Ser. No. 10/017,836, filed Dec. 12, 2001, titled DYNAMIC CONTROL OF OVERDRIVE PACING BASED ON DEGREE OF RANDOMNESS WITHIN HEART RATE; and Ser. No. 10/017,837, filed Dec. 12, 2001, titled DYNAMIC CONTROL OF OVERDRIVE PACING BASED ON DEGREE OF RANDOMNESS WITHIN HEART RATE.

FIELD OF THE INVENTION

The invention generally relates to implantable cardiac stimulation devices such as pacemakers or implantable cardioverter defibrillators (ICDs) and, in particular, to techniques for predicting the likelihood of a tachyarrhythmia and for controlling overdrive pacing to prevent such an arrhythmia.

BACKGROUND OF THE INVENTION

An arrhythmia is an abnormal heart rhythm. One example of an arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia, the atria of the heart beat abnormally fast. With ventricular tachycardia, the ventricles of the heart beat abnormally fast. Though often unpleasant for the patient, an atrial tachycardia is typically not fatal. However, some tachycardia, particularly ventricular tachycardia, can trigger ventricular fibrillation wherein the heart beats chaotically resulting in little or no net flow of blood from the heart to the brain and other organs. Ventricular tachycardia and ventricular fibrillation, if not terminated, are fatal. Hence, it is highly desirable to prevent or terminate arrhythmias, particularly ventricular tachycardia.

One technique for preventing arrhythmias is to overdrive pace the heart wherein an implantable cardiac stimulation device, such as a pacemaker or ICD, applies electrical pacing pulses to the heart at a rate somewhat faster than the intrinsic heart rate of the patient having a normal sinus rhythm. For bradycardia, the cardiac stimulation device may be programmed to pace the heart at a rate of 60 to 80 pulses per minute (ppm) to thereby prevent the heart from beating too slow and to eliminate any long pauses between heartbeats. To prevent tachyarrhythmias from occurring, the cardiac stimulation device paces the heart at a rate slightly faster than the intrinsic heart rate of the patient.

In one exemplary technique, the cardiac stimulation device monitors the heart of the patient and, if two consecutive intrinsic heartbeats are detected (or two intrinsic beats are detected within a predetermined number of cycles), overdrive pacing is automatically triggered. The overdrive pacing rate is typically set to 5 to 10 ppm higher than the intrinsic rate. The intrinsic heart rate may be determined, for example, by calculating the time interval between the two consecutive intrinsic beats—typically the interval between two consecutive intrinsic P-waves or two consecutive intrinsic R-waves. The stimulation device then overdrive paces the heart at the overdrive pacing rate for a "dwell period" equal to a programmed number of overdrive events or cycles. Thereafter, the stimulation device decreases the overdrive pacing rate by a rate decrement specified by a programmed "recovery rate" until additional intrinsic beats are detected, then the device repeats the process to determine a new overdrive pacing rate and paces accordingly.

It is believed that overdrive pacing is effective for at least some patients for preventing the onset of an actual tachycardia for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can trigger a tachycardia. By overdrive pacing the heart, the likelihood of the occurrence of ectopic pulses is reduced and the risk of tachycardia may be substantially reduced.

Thus it is desirable within patients prone to tachyarrhythmia to overdrive pace the heart in an attempt to prevent a tachyarrhythmia from occurring. Ideally, overdrive pacing is performed only prior to an expected episode of tachyarrhythmia, rather than continuously. Continuous overdrive pacing is preferably not employed because it may be unpleasant to the patient. The higher heart rate caused by continuous overdrive pacing may also cause damage to the heart or trigger more a serious arrhythmia, such as ventricular fibrillation. Continuous overdrive pacing may be especially problematic in patients suffering from heart failure, particularly if the heart failure is due to an impaired diastolic function. Continuous overdrive pacing may actually exacerbate heart failure in these patients. Also, continuous overdrive pacing may be a problem in patients with coronary artery disease because increasing the heart rate decreases diastolic time and decreases perfusion, thus intensifying ischemia. Moreover, the need to continuously apply overdrive pacing pulses can deplete the power supply of the stimulation device, necessitating surgical replacement of the device on a more frequent basis.

Thus it would be highly desirable to provide a technique for predicting the onset of an episode of tachyarrhythmia so that overdrive pacing can be initiated prior to the tachyarrhythmia in attempt to prevent the tachyarrhythmia from actually occurring. Heretofore, however, no reliable techniques have been developed for predicting the onset of a tachyarrhythmia. Accordingly, it would be desirable to provide a technique for predicting the onset of a tachyarrhythmia, particularly atrial fibrillation, and aspects of the invention are directed to that end. Other aspects of the invention are directed to providing systems and methods for controlling pacing so as to reduce the risk of the tachyarrhythmia.

SUMMARY OF THE INVENTION

In accordance with a first aspect of the invention, a technique is provided for predicting the onset of a tachyarrhythmia based on a degree of randomness in the heart rate of the patient. The degree of randomness is determined, for example, by calculating the degree of entropy, chaos dimensionality, or spectral coefficient associated with the heart rate. If the degree of randomness falls below a predetermined threshold value, there is a significant risk of onset of a tachyarrhythmia and appropriate prophylactic steps are taken, such as aggressive overdrive pacing.

In accordance with a second aspect of the invention, a technique is provided for controlling overdrive pacing based, in part, on the degree of randomness in the heart rate of the patient. In one example, if the degree of randomness falls below a predetermined threshold value, the aggressiveness of overdrive pacing that has already begun is increased, either by raising the overdrive pacing rate, raising the overdrive pacing dwell time, or lowering the overdrive pacing rate recovery decrement. In this manner, a potential tachyarrhythmia may be avoided.

In accordance with a third aspect of the invention, a technique is provided for increasing the degree of randomness within the heart rate by chaotic pacing. In one example, pacing parameters are controlled so as to continuously vary intervals between consecutive P-waves to thereby increase the overall degree of randomness in the heart rate in an effort to prevent the heart from lapsing into a coherent state in which a tachyarrhythmia is likely.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

Figure 1:
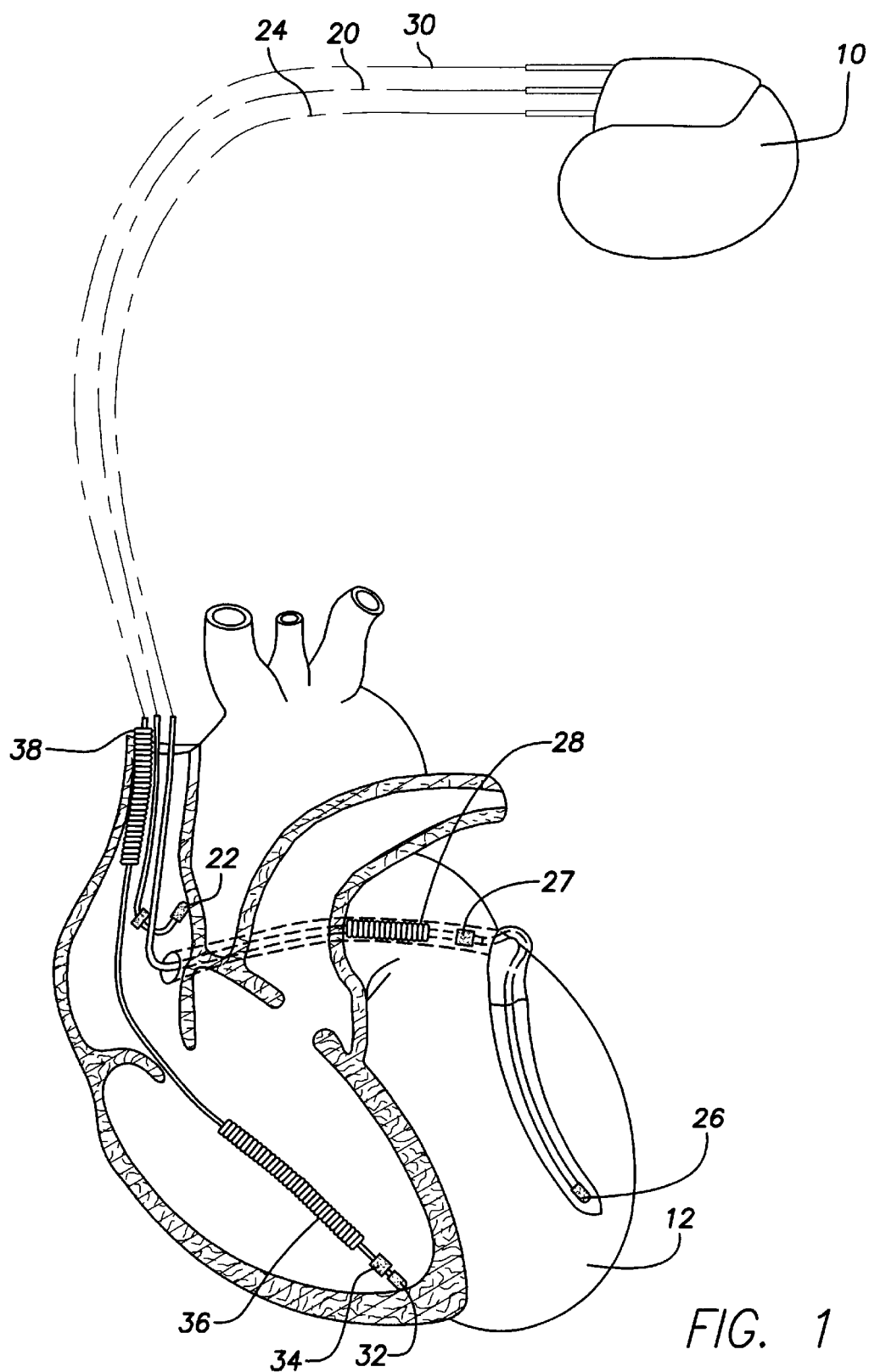
FIG. 1 is a simplified diagram illustrating an implantable cardiac stimulation device in electrical communication with at least three leads implanted into the heart of a patient for delivering multi-chamber stimulation and shock therapy and configured in accordance with the invention to pace the heart based on a degree of randomness in the heart rate of the patient.

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.
Stimulation Device As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
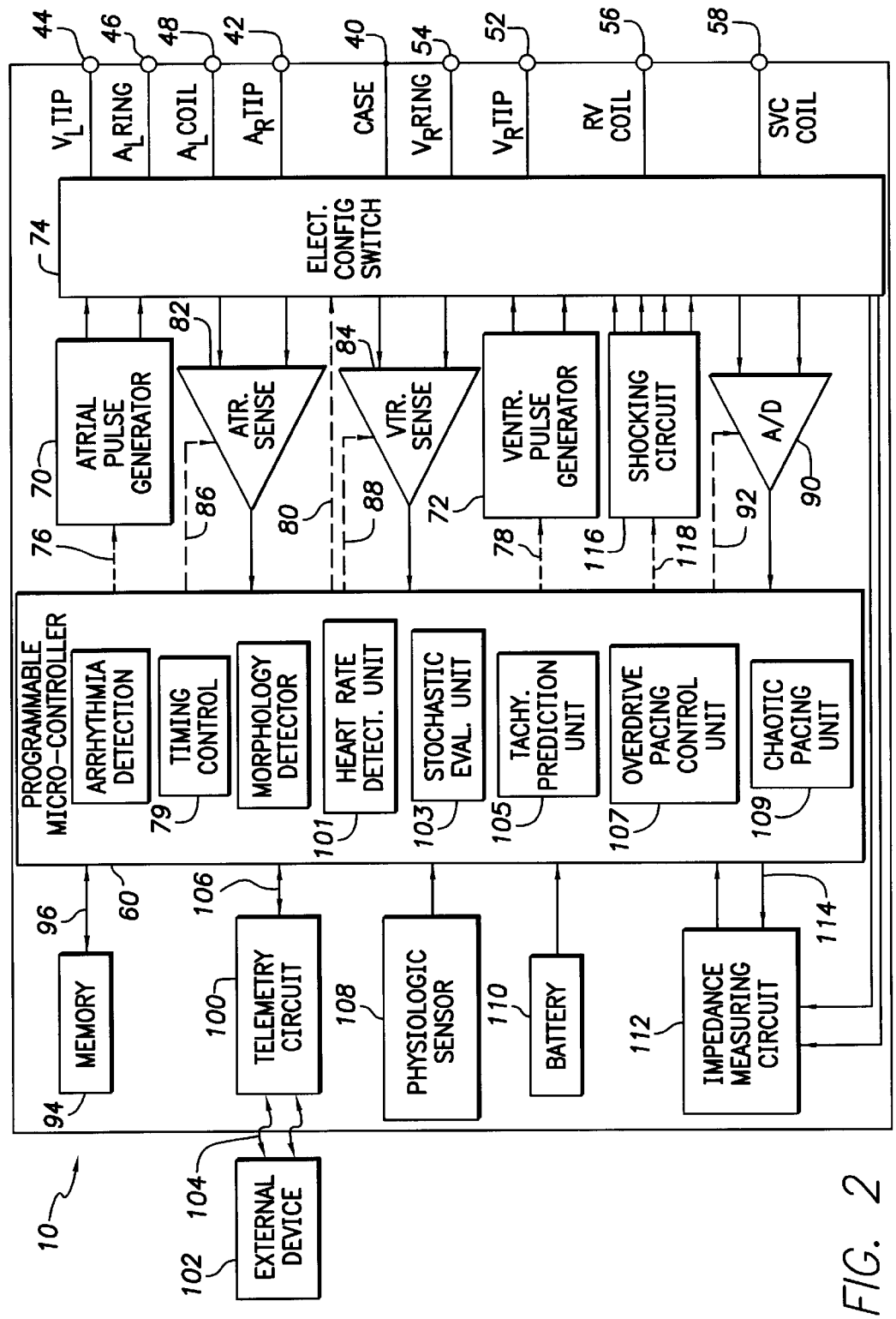
FIG. 2 is a functional block diagram of the implantable cardiac stimulation device of FIG. 1 illustrating basic elements of the stimulation device.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art. Representative types of control circuitry that may be used with the invention include the microprocessor-based control system of U.S. Pat. No. 4,940,052 (Mann et al.), the state-machine of U.S. Pat. Nos. 4,712,555 (Sholder) and 4,944,298 (Sholder).

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. For the various dynamic atrial overdrive pacing techniques described below, the ventricular pacing components are not typically needed. Ventricular pacing components are shown in FIGS. 1 and 2 for the sake of completeness.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

Stimulation device 10 further includes a rate-responsive sensor 108 used to adjust a pacing stimulation rate according to the exercise state or degree of activity of the patient. The rate-responsive sensor may be any sensor capable of generating a signal for use in performing rate-responsive pacing. Sensor 108 may be, for example, a physiological sensor for determining a physiological characteristic of the patient, such as a minute ventilation sensor, vasovagal syncope sensor or other sensors which sense the oxygen content of blood, respiration rate, pH of the blood, ventricular gradient, etc. As another example, sensor 108 may be an orthostatic sensor for determining a degree of activity of the patient based on the orientation of the patient, i.e. whether the patient is lying down or standing. Sensor 108 may be a sensor that generates values representative of the degree of exercise of the patient based on an analysis of electrical signals in the heart, such as a paced depolarization integral sensor. Sensor 108 may alternatively be configured to detect changes in cardiac output, changes in the physiological condition of the heart, or diurnal changes in activity (e.g., detecting sleep and wake states). Sensor 108 may be a physical activity sensor, such as an accelerometer or a piezoelectric crystal, which detects the motion of the patient. The physical activity sensor may be employed in conjunction with an "activity variance" sensor, which monitors the activity sensor diurnally to detect the low variance in the measurement corresponding to the sleep state. For a complete description of an activity variance sensor, see U.S. Pat. No. 5,476,483 (Bornzin et. al), issued Dec. 19, 1995 which patent is hereby incorporated by reference. While shown as being included within the stimulation device 10, it is to be understood that the rate-responsive sensor 108 may also be external to the stimulation device 10, yet still be implanted within or carried by the patient.

In general, any sensor (or combination of sensors) may be used which is capable of generating a parameter that corresponds to the exercise state or degree of activity of the patient. Two or more rate-responsive sensors may be employed in combination. The signal or signals generated by the sensors are processed by the microcontroller to determine a sensor indicated rate for the patient.

Also included within the microcontroller are a heart rate detection unit 101, stochastic evaluation unit 103, a tachyarrhythmia prediction unit 105, an overdrive pacing control unit 107, and a chaotic pacing unit 109. The stochastic evaluation unit determines a degree of randomness in the heart based on the entropy, chaos dimensionality, spectral coefficient, or mean and standard deviation in P—P durations. The tachyarrhythmia prediction unit evaluates the likelihood of onset of tachyarrhythmia based on the degree of randomness to, for example, generate a warning signal if there is a substantial risk of the tachyarrhythmia. The overdrive pacing control unit controls overdrive pacing based on the degree of randomness to, for example, increase the aggressiveness of overdrive pacing to avert a tachyarrhythmia. The chaotic pacing unit operates to control pacing of the heart so as to increase the degree of randomness in the heart rate so as to prevent the heart from settling into a state which might result in a an increased risk of a tachyarrhythmia. These units will be described in greater detail below.

The stimulation device additionally includes a battery 110 that provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 4, the device 10 is shown as having an impedance measuring circuit 112 which is enabled by the microcontroller 60 via a control signal 114.

In the case where the stimulation device 10 is intended to operate as an ICD device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
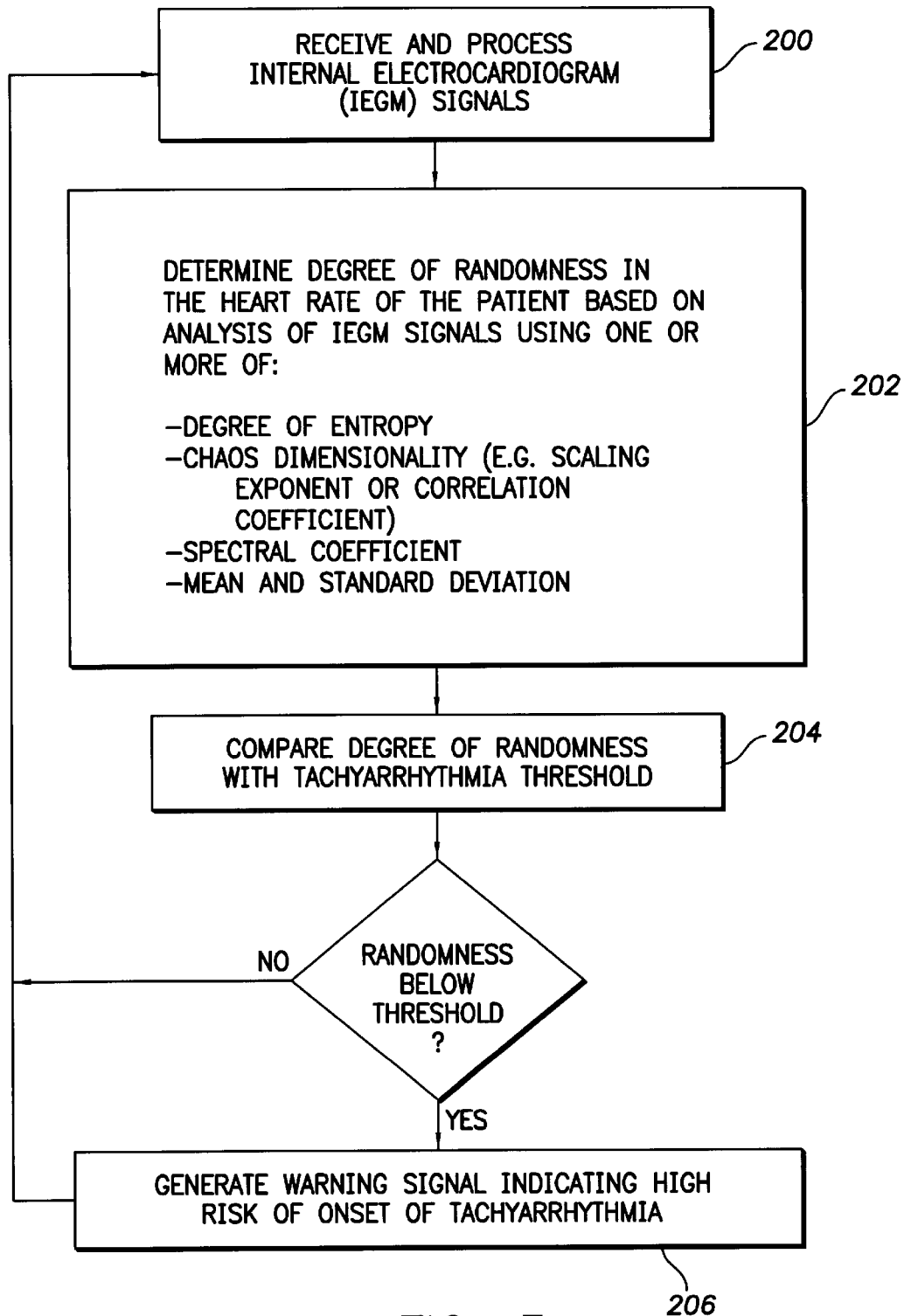
FIG. 3 is a flow chart providing an overview of the first aspect of the invention wherein the stimulation device of FIGS. 1 and 2 predicts the risk of onset of a tachyarrhythmia based on the degree of randomness in the heart rate.

Prediction of Likelihood of Tachyarrhythmia Based on Degree of Randomness in Heart Rate Referring next to FIG. 3, a flow chart is shown describing an overview of the operation and novel features of stimulation device 10 as configured in accordance with a first embodiment of the invention. In this flow chart, and the other flow charts described herein, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Briefly, the technique of FIG. 3 operates to evaluate the likelihood of onset of a tachyarrhythmia based on the degree of randomness in the heart rate of the patient. If the heart rate is not sufficiently random, that is the heart rate is too uniform or coherent, there is a higher risk of tachyarrhythmia. The degree of randomness may be determined, for example, by tracking variations in P—P intervals of the heart rate from one beat to another. The technique exploits the recognition that a certain degree of randomness is typically necessary in the heart rate of a patient to prevent the onset of a tachyarrhythmia, at least within certain patients prone to tachyarrhythmias. If the heart rate becomes too uniform, that uniformity can trigger a tachyarrhythmia. Hence, the degree of randomness appears to be a useful predictor of the likelihood of at least certain types of tachyarrhythmias within these patients.

Beginning at step 200, the heart rate detection unit (101 of FIG. 2) begins receiving and processing IEGM signals to, for example, identify P-waves, R-waves, and T-waves therein. At step 202, the stochastic evaluation unit 103 analyzes the processed heart signals to determine a degree of randomness associated with the heart rate of the patient. The degree of randomness may be determined based on one or more of:

the degree of entropy in the heart rate the chaos dimensionality associated with the heart rate (based on, for example, scaling exponent or correlation dimension)

a spectral coefficient associated with the heart rate the mean and standard deviation in the heart rate.

The tachyarrhythmia prediction unit (105 of FIG. 2) then compares the degree of randomness with a predetermined numerical randomness threshold at step 204 and, if it exceeds the threshold, indicating that the heart rate is sufficiently random, processing simply returns to step 200 for continued monitoring of the heart rate of the patient. If, however, the degree of randomness is not sufficiently high, indicating that the heart may be prone to tachyarrhythmia, then a warning signal is generated, at step 206. As will be explained below, if the risk of a tachyarrhythmia is high, the overdrive pacing unit then initiates overdrive pacing in an attempt to prevent the tachyarrhythmia or, if overdrive pacing has already commenced, the overdrive pacing unit increases the aggressiveness of overdrive pacing. Additionally or alternatively, the warning signal is output to the patient by transmitting the signal to an external indicator device or, if the pacemaker is so equipped, by causing the pacemaker to vibrate. Thus alerted, the patient then takes appropriate steps to prevent the tachyarrhythmia by, for example, ceasing any vigorous physical activity. In still other embodiments, the warning signal is recorded within the pacemaker as diagnostic information for eventual output to an external programmer device to permit a physician or researcher to evaluate the circumstances that triggered the warning signal and to determine whether the warning was appropriate, i.e. to verify that a tachyarrhythmia did in fact subsequently occur. Hence, the warning signal can be used as a valuable diagnostic and research tool.

Insofar as the threshold value is concerned, rather than providing a single threshold value, a set of tiered threshold values can be defined, with a higher risk of tachyarrhythmia associated with the each threshold value. Multiple techniques for calculating the degree of randomness can be employed simultaneously, each compared against separate threshold values. The warning signal is then triggered, depending upon the programming of the system, if any one of the calculated randomness values falls below its corresponding threshold value or if each of the calculated randomness values falls below its corresponding threshold value. Alternatively, the separately calculated randomness values are combined with on another (with appropriate weighting) then compared against a single threshold metric. As can be appreciated, a wide variety of threshold comparison techniques can be employed with the invention.

Appropriate threshold values are determined in advance, for example, by tracking the degree of randomness within heart rates of an entire population of patients prone to tachyarrhythmia then correlating the degree of randomness with the actual onset of tachyarrhythmias. A statistical analysis of the correlated data is performed to determine specific thresholds values corresponding to particular risk levels of the tachyarrhythmia. For example, the degree of randomness sufficient to yield a 75% risk of onset of a tachyarrhythmia with then next fifteen minutes can be statistically determined then used as the threshold value within the pacemaker. Preferably the physician is permitted to program the pacemaker to generate the warning signal based on a selected risk factor, such as 50%, 75%, 90%, etc. Alternatively, rather than determining the threshold values based on a statistical analysis of an entire population of patients, the threshold value can be automatically determined by the pacemaker itself by tracking the degree of randomness within the heart rate of the patient in which the pacemaker is implanted then correlating the degree of randomness with the actual onset of tachyarrhythmias within the patient. After a statistically sufficient number of episodes of tachyarrhythmia have occurred, the pacemaker automatically sets the threshold value to a pre-programmed risk factor, such as 75%. In general, a wide variety of techniques can be employed for setting and adjusting the threshold values and no attempt is made herein to list all possible techniques.

As noted, the stochastic evaluation unit 103 calculates the degree of randomness based on one or more of: degree of entropy in the heart rate; degree of chaos; spectral coefficient; or mean and standard deviation in the heart rate.

The degree of entropy is determined using otherwise conventional entropy calculation techniques applied to the P—P intervals, R—R intervals, or other appropriate indicators of heart rate. Exemplary techniques for calculating entropy based on R—R intervals are described in "Abnormalities in Beat to Beat Complexity of Heart Rate Dynamics in Patients with a Previous Myocardial Infraction", Makikallio et al., *Journal of American College of Cardiology* Vol. 28. No 4. October 1996:1005–11. More specifically the article describes techniques for computing a statistical estimate of approximate entropy based on a time series of R—R values. See also "Approximate Entropy as a Measure of System Complexity", Pincus, *Proc. Natl. Acad. Sci. USA* Vol. 88, pp 2297–2301, March 1991. These articles are incorporated by reference herein.

Chaos dimensionality is determined using otherwise conventional scaling exponent calculation techniques applied to P—P intervals or other appropriate indicators of heart rate. Techniques for calculating a scaling exponent (also referred to as a "self similarity exponent" or "scaling factor") from heart rate data are described in "Quantification of Scaling Exponents and Crossover Phenomena in Non-stationary Heartbeat Time Series", C.-K. Peng et al., *Chaos*, Vol. 5, No. 1, pp 82–87. In the alternative, chaos dimensionality can be determined using otherwise conventional correlation dimension calculation techniques. Techniques for calculating a correlation dimension from heart rate data are described in "Slope Filtered Pointwise Correlation Algorithm and Its Evaluation with Prefibrillation Heart Rate Data", Kroll and Fulton, *Journal of Electrocardiology*, Vol. 24 Supplement, pp 97–101 (1991). See also "Signal and Image Analysis Using Chaos Theory and Fractal Geometry", *Machine Graphics & Vision*, Vol. 9(1/2), pp 403–431, (2000) and Scaling Exponent Predicts Defibrillation Success for Out-of-Hospital Ventricular Fibrillation Cardiac Arrest", Callaway et al., *Circulation*, pp 1656–1661, Mar. 27, 2001. These articles are incorporated by reference herein.

A suitable technique for calculating spectral coefficients is to use a fast Fourier transform (FFT). Techniques for calculating mean and standard deviation may be entirely conventional as well.

Control of Overdrive Pacing Based on Degree of Randomness in Heart Rate

Figure 4:
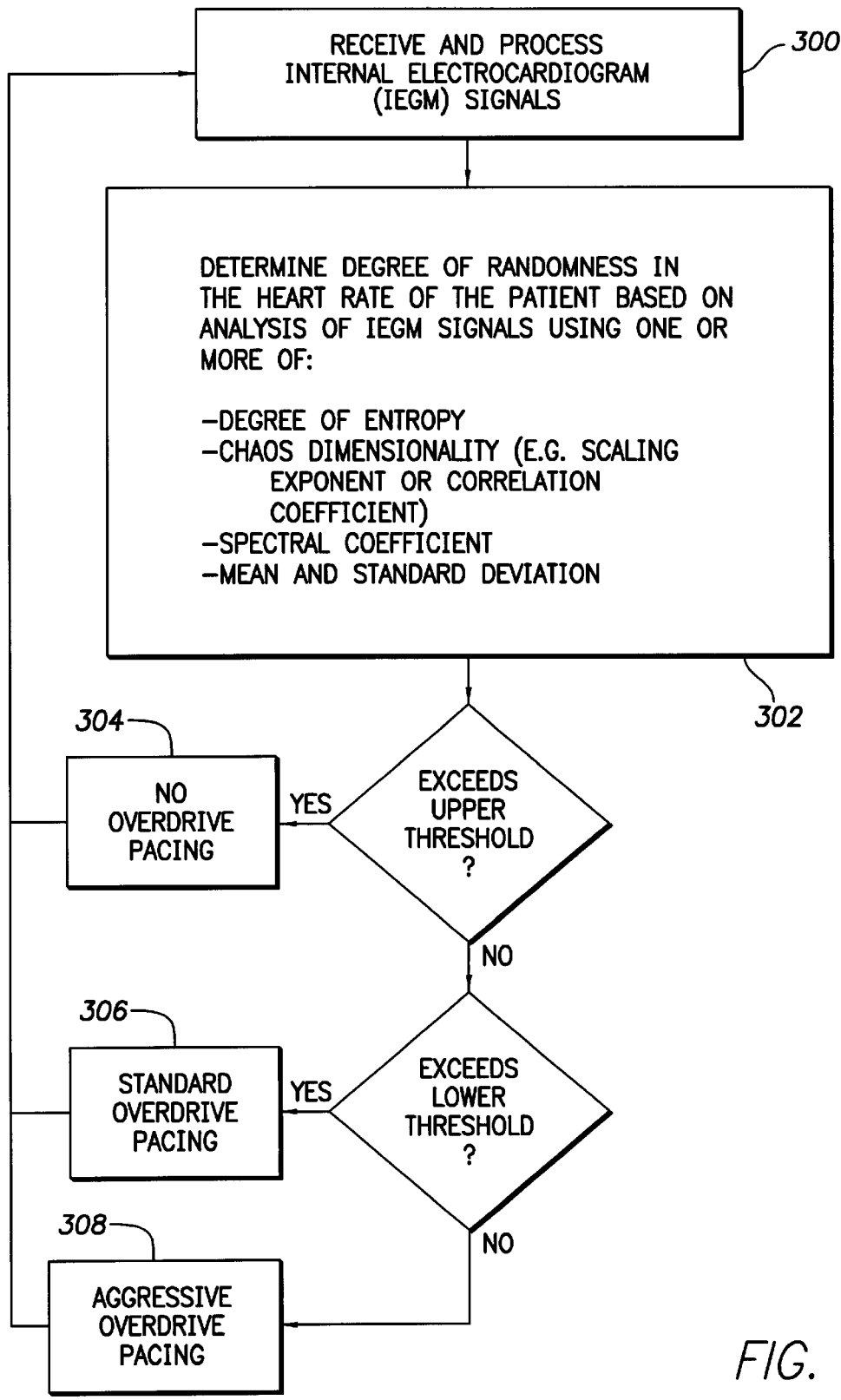
FIG. 4 is a flow chart providing an overview of the second aspect of the invention wherein the stimulation device controls overdrive pacing based on the degree of randomness in the heart rate in an effort to prevent the tachyarrhythmia.

Referring next to FIG. 4, a flow chart is shown describing an overview of the operation and novel features of stimulation device 10 as configured in accordance with a second embodiment of the invention. Briefly, the technique of FIG. 4 operates to control overdrive pacing based on the degree of randomness in heart rate of the patient.

At step 300, the heart rate detection unit (101 of FIG. 2) receives IEGM signals and, at step 302, the stochastic evaluation unit (103 of FIG. 2) determines the degree of randomness associated with the heart rate in the manner described above based on one or more of: degree of entropy in the heart rate; degree of chaos; spectral coefficient; or mean and standard deviation in the heart rate.

Then, overdrive pacing control unit (107 of FIG. 2) compares the degree of randomness with a pair of upper and lower numerical threshold values. If the degree of randomness exceeds the upper threshold, no overdrive pacing is performed, step 304. If the degree of randomness falls between the upper and lower thresholds, indicating that the heart may be prone to tachyarrhythmia, standard overdrive pacing is initiated in an effort to prevent the tachyarrhythmia, step 306. If the degree of randomness falls below the lower threshold, indicating a higher risk of tachyarrhythmia, aggressive overdrive pacing is initiated, step 308. As noted above, it is believed that overdrive pacing is effective for at least some patients for preventing the onset of tachyarrhythmia. Hence, standard overdrive pacing is initiated in circumstances wherein a tachyarrhythmia is somewhat likely to occur and aggressive overdrive pacing is initiated in circumstances wherein the tachyarrhythmia is highly likely to occur. The upper threshold may be set, for example, to a degree of randomness yielding a 75% risk factor and the lower threshold may be set, for example, to a degree of randomness yielding a 90% risk factor.

Standard overdrive pacing is performed by setting the overdrive pacing rate to a standard level, such as 5 ppm above the current intrinsic heart rate. Aggressive overdrive pacing is performed by setting the overdrive pacing rate to a more aggressive level, such as 15 ppm above the current intrinsic heart rate. The aggressiveness of the overdrive pacing can also be varied by adjusting the recovery rate, i.e. the rate at which the overdrive pacing rate is automatically reduced following a sequence of pacing pulses so as to detect intrinsic heart beats or by resetting the dwell time, that is the number of beats paced at the overdrive rate before rate recovery begins.

Figure 5:
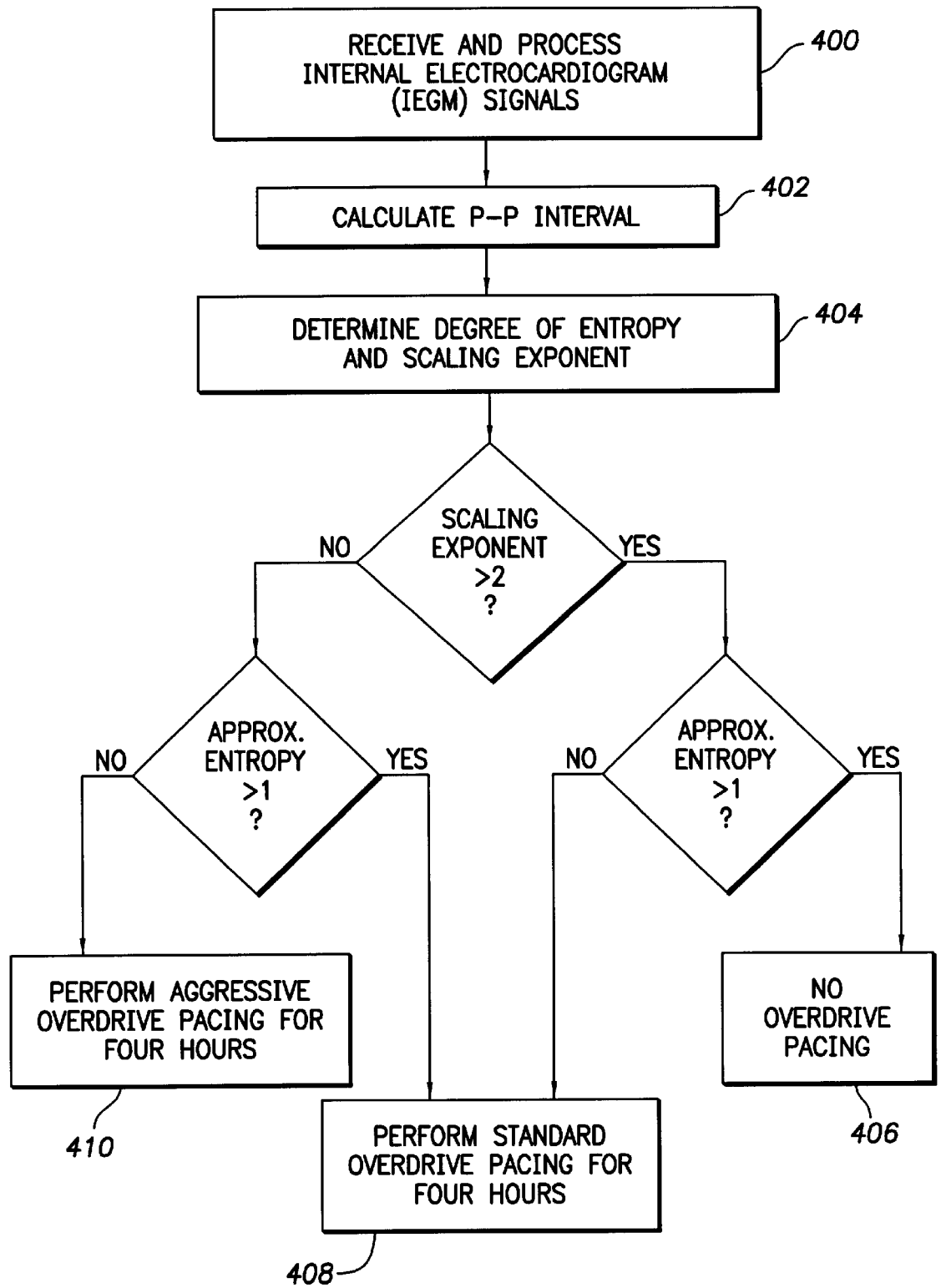
FIG. 5 is a flow chart providing an overview of an alternative technique to that of FIG. 4 for controlling overdrive pacing based on the degree of randomness in the heart rate.

Several techniques can simultaneously be employed for calculating degree of randomness of the heart rate for comparison against separate threshold values. An exemplary technique employing both a scaling exponent and approximate entropy is provided in FIG. 5. At step 400, the heart rate detection unit (101 of FIG. 2) receives IEGM signals and, at step 402, calculates and stores P—P intervals. At step 404, the stochastic evaluation unit (103 of FIG. 2) calculates both a scaling exponent and approximate entropy based on the P—P values in accordance with techniques referenced above. If the scaling exponent exceeds a scaling threshold value of 2 and the approximate entropy exceeds an approximate entropy threshold value of 1, no overdrive pacing is performed, step 406. If the scaling exponent exceeds the scaling threshold but the approximate entropy does not exceed the approximate entropy threshold, standard overdrive pacing is performed, step 408. Also, if the scaling exponent falls below the scaling threshold but the approximate entropy exceeds the approximate entropy threshold, standard overdrive pacing is likewise performed, step 408. Finally, if the scaling exponent falls below the scaling threshold and the approximate entropy also falls below the correlation threshold, aggressive overdrive pacing is performed, step 410.

Chaotic Overdrive Pacing

Figure 6:
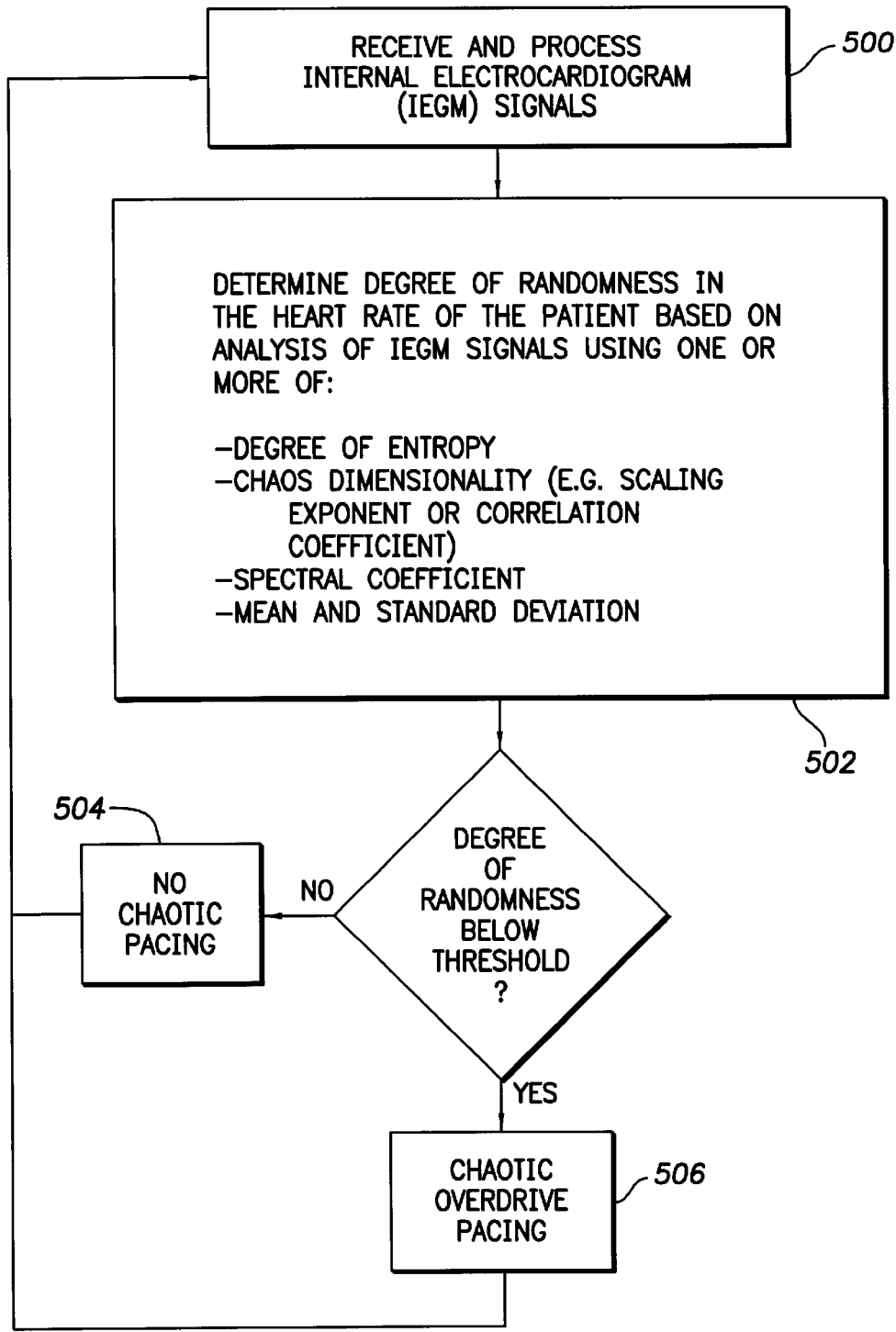
FIG. 6 is a flow chart providing an overview of the third aspect of the invention wherein the stimulation device performs chaotic pacing to reduce the risk of a tachyarrhythmia.

Referring next to FIG. 6, a flow chart is shown describing an overview of the operation and novel features of stimulation device 10 as configured in accordance with a third embodiment of the invention. Briefly, the technique of FIG. 6 operates to perform chaotic pacing if the degree of randomness in heart rate of the patient is found to be too low.

As with the previous techniques, at step 500, the heart rate detection unit (101 of FIG. 2) receives IEGM signals and, at step 502, the stochastic evaluation unit (103 of FIG. 2) determines the degree of randomness associated with the heart rate based on one or more of: degree of entropy in the heart rate; degree of chaos; spectral coefficient; or mean and standard deviation in the heart rate. The chaotic pacing unit (109 of FIG. 2) then compares the degree of randomness with a predetermined threshold value and, if it exceeds the threshold, indicating that the heart has naturally achieved a sufficient degree of randomness, chaotic pacing is not performed, step 504. Depending upon the programming of the device, standard overdrive pacing may instead be performed, or perhaps no pacing whatsoever is performed. If, however, the degree of randomness falls below the threshold, chaotic pacing is initiated, step 506, so as to increase the degree of randomness in the heart rate. In this manner, the degree of randomness is maintained at a level sufficient to reduce the risk of onset of a tachyarrhythmia. In one example, the threshold value is set to a risk factor of 1% such that, so long as the degree of randomness is maintained above that level by chaotic pacing, there is only a 1% risk of onset of a tachyarrhythmia.

Chaotic pacing is performed, for example, by overdrive pacing the heart while varying the overdrive pacing rate throughout each overdrive pacing dwell period. Preferably, the overdrive rate is varied within a range set to minimize intrinsic beats. For example, the over drive rate may be varied between 10 and 20 ppm above the intrinsic rate through the dwell period. Once the dwell period has elapsed, conventional rate recovery techniques are employed to reduce the overdrive rate until additional intrinsic beats are detected. By varying the overdrive rate during each dwell period, a significant increase in heart rate variability is achieved. Alternatively, otherwise conventional overdrive pacing techniques are employed wherein the overdrive rate remains constant during each dwell time but the overdrive rate, dwell time, or rate recovery value are randomly adjusted just prior to each new instance of overdrive pacing. By adjusting the overdrive pacing parameters, a general increase in heart rate variability is achieved. In yet another alternative technique, chaotic pacing is performed without using overdrive pacing by, for example, tracking the intrinsic rate and occasionally stimulating the heart prior to a next expected intrinsic beat. As can be appreciated, a wide variety of techniques can be employed with the invention for increasing heart rate variability via chaotic pacing so as to reduce the likelihood of a tachyarrhythmia. No attempt is made herein to list all possible techniques, but many other techniques will be readily apparent to those skilled in the art.

What have been described are various techniques for predicting the likelihood of the onset of a tachyarrhythmia and for controlling pacing in an attempt to prevent tachyarrhythmias from occurring. The techniques may be applied to ventricular pacing as well as atrial pacing. Also, although described primarily with reference to an example wherein the implanted device is an ICD, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device for implant within a patient wherein the device comprises an overdrive pacing unit, a method comprising:

receiving signals representative of the heart rate of the patient;

determining a degree of randomness in the heart rate of the patient; and controlling overdrive pacing based on the degree of randomness in the heart rate and a threshold value.

2. The method of claim 1 wherein controlling overdrive pacing based on the degree of randomness comprises:

comparing the degree of randomness in the heart rate with said threshold value; and activating overdrive pacing if the degree of randomness falls below a predetermined threshold.

3. The method of claim 1 wherein controlling overdrive pacing based on the degree of randomness comprises:

comparing the degree of randomness in the heart rate with said threshold value; and increasing overdrive pacing if the degree of randomness falls below a predetermined threshold.

4. The method of claim 3 wherein increasing overdrive pacing comprises increasing an overdrive pacing rate.

5. The method of claim 3 wherein increasing overdrive pacing comprises increasing an overdrive pacing dwell time.

6. The method of claim 3 wherein increasing overdrive pacing comprises decreasing an overdrive pacing rate recovery decrement.

7. The method of claim 1 wherein controlling overdrive pacing based on the degree of randomness comprises:

varying overdrive pacing control parameters so as to increase the degree of randomness in the heart rate.

8. The method of claim 7:

wherein determining a degree of randomness in the heart rate of the patient comprises determining a degree of entropy associated with the heart rate and calculating a value representative of the degree of randomness based on the degree of entropy; and wherein controlling overdrive pacing the heart so as to increase a degree of randomness in the heart rate comprises varying overdrive pacing control parameters so as to effect an increase in the degree of entropy associated with the heart rate.

9. The method of claim 7:

wherein determining a degree of randomness in the heart rate of the patient comprises determining a degree of chaos associated with the heart rate and calculating a value representative of the degree of randomness based on the degree of chaos; and wherein controlling overdrive pacing the heart so as to increase a degree of randomness in the heart rate comprises varying overdrive pacing control parameters so as to effect an increase in the degree of chaos associated with the heart rate.

10. The method of claim 7:

wherein determining a degree of randomness in the heart rate of the patient comprises determining a spectral coefficient associated with the heart rate and calculating a value representative of the degree of randomness based on the spectral coefficient; and wherein controlling overdrive pacing the heart so as to increase a degree of randomness in the heart rate comprises varying overdrive pacing control parameters so as to effect an increase in the spectral coefficient associated with the heart rate.

11. The method of claim 7:

wherein determining a degree of randomness in the heart rate of the patient comprises determining a mean and standard deviation in the heart rate and calculating a value representative of the degree of randomness based on the mean and standard deviation; and wherein controlling overdrive pacing the heart so as to increase a degree of randomness in the heart rate comprises varying overdrive pacing control parameters so as to effect an increase in the standard deviation of the heart rate.

12. The method of claim 1 further comprising determining a value representative of the likelihood of onset of a tachyarrhythmia based on the degree of randomness in the heart rate.

13. The method of claim 12 wherein determining the value representative of the likelihood of onset of a tachyarrhythmia comprises:

comparing the degree of randomness in the heart rate with said threshold value; and generating a signal indicative of the onset of a tachyarrhythmia if the degree of randomness falls below the threshold value.

14. In an implantable cardiac stimulation device for implant within a patient, a system comprising:

a heart rate detection unit;

an evaluation unit that is operative to determine a degree of randomness in the heart rate; and an overdrive pacing control unit operative to overdrive pace the heart based on the degree of randomness in the heart rate and a threshold value.

15. The system of claim 14 wherein the evaluation unit is operative to determine a degree of entropy associated with heart rate and to calculate a value representative of the degree of randomness based on the degree of entropy.

16. The system of claim 14 wherein the evaluation unit is operative to determine a degree of chaos associated with heart rate and to calculate a value representative of the degree of randomness based on the degree of chaos.

17. The system of claim 14 wherein the evaluation unit is operative to determine a spectral coefficient associated with the heart rate and to calculate a value representative of the degree of randomness based on the spectral coefficient.

18. The system of claim 14 wherein the evaluation unit is operative to determine a mean and standard deviation in the heart rate and
to calculate a value representative of the degree of randomness based on the mean and standard deviation.

19. The system of claim 14 wherein the overdrive pacing control unit is operative to compare the degree of randomness in the heart rate with said threshold value and to activate overdrive pacing if the degree of randomness falls below a predetermined threshold.

20. The system of claim 14 wherein the overdrive pacing control unit is operative to compare the degree of randomness in the heart rate with said threshold value and to increase overdrive pacing if the degree of randomness falls below a predetermined threshold.

21. The system of claim 14 wherein the overdrive pacing control unit is operative to vary overdrive pacing control parameters so as to increase the degree of randomness in the heart rate.

22. In an implantable cardiac stimulation device for implant within a patient, a system comprising:
   means for receiving signals representative of the heart rate of the patient;
   means for determining a degree of randomness in the heart rate of the patient; and
   means for controlling overdrive pacing based on the degree of randomness in the heart rate and a threshold value.

23. In an implantable cardiac stimulation device, a method comprising:
   receiving signals that are representative of a heart rate of a patient;
   determining a degree of randomness in the heart rate;
   comparing the degree of randomness with a predefined threshold; and
   initiating overdrive pacing if the degree of randomness falls below the threshold value.

* * * * *